United States Patent
Li et al.

(10) Patent No.: US 12,428,367 B2
(45) Date of Patent: Sep. 30, 2025

(54) METHODS FOR SEPARATING THE BINARY AZEOTROPIC MIXTURE OF ETHYLENE GLYCOL AND ETHYLENE GLYCOL DIACETATE WITH SULFOLANE ENTRAINER

(71) Applicant: CHANGZHOU UNIVERSITY, Jiangsu (CN)

(72) Inventors: Jiashu Li, Changzhou (CN); Jinlong Li, Changzhou (CN); Fang Wang, Changzhou (CN)

(73) Assignee: CHANGZHOU UNIVERSITY, Changzhou (CN)

( * ) Notice: Subject to any disclaimer, the term of this patent is extended or adjusted under 35 U.S.C. 154(b) by 0 days.

(21) Appl. No.: 19/022,985

(22) Filed: Jan. 15, 2025

(65) Prior Publication Data

US 2025/0154093 A1 May 15, 2025

Related U.S. Application Data

(63) Continuation-in-part of application No. PCT/CN2023/107635, filed on Jul. 17, 2023.

(30) Foreign Application Priority Data

Jul. 18, 2022 (CN) .......................... 202210842945.2

(51) Int. Cl.
C07C 67/54 (2006.01)
C07C 29/82 (2006.01)

(52) U.S. Cl.
CPC .............. *C07C 67/54* (2013.01); *C07C 29/82* (2013.01)

(58) Field of Classification Search
CPC .......... C07C 67/54; C07C 29/82; Y02P 20/10
See application file for complete search history.

(56) References Cited

U.S. PATENT DOCUMENTS

| 3,809,724 | A | * | 5/1974 | Golden ................... C07C 29/82 |
| | | | | 203/84 |
| 4,525,245 | A | | 6/1985 | Berg et al. |
| 4,601,791 | A | | 7/1986 | Berg et al. |
| 5,393,385 | A | * | 2/1995 | Berg ....................... C07C 67/54 |
| | | | | 585/864 |

FOREIGN PATENT DOCUMENTS

| CN | 103183609 | A | | 7/2013 |
| CN | 109369396 | A | | 2/2019 |
| CN | 115160109 | | * | 10/2022 |
| CN | 115160109 | A | | 10/2022 |

OTHER PUBLICATIONS

CN115160109 translation 2022 (Year: 2022).*
International Search Report in PCT/CN2023/107635 mailed on Oct. 19, 2023, 6 pages.
Written Opinion in PCT/CN2023/107635 mailed on Oct. 19, 2023, 6 pages.
Wang, Fang et al., Research on Thermodynamic Properties of Binary Mixture of Ethylene Glycol and Ethylene Glycol Diacetate, Chemical Reaction Engineering and Technology, 37(1): 39-40, 2021.
Lloyd Berg et al., The separation of lower boiling alcohols by extractive distillation, Chemical Engineering Communications, 66: 1-21, 1988.

* cited by examiner

*Primary Examiner* — Andrew D Kosar
*Assistant Examiner* — Blaine G Doletski
(74) *Attorney, Agent, or Firm* — PORUS IP LLC

(57) ABSTRACT

Method for separating ethylene glycol (EG) and ethylene glycol diacetate (EGDA) with sulfolane entrainer, including: obtaining EG and a mixture of EGDA and sulfolane through separating a mixture of EG and EGDA under an action of sulfolane by an extractive distillation tower; obtaining EGDA and sulfolane through separating the mixture of the EGDA and the sulfolane by an entrainer recovery tower; and obtaining recycled sulfolane through cooling the sulfolane by a heat exchanger, and mixing the recycled sulfolane with fresh sulfolane and circulating into the extractive distillation tower for recycling. Through the method, a yield of the EG is greater than or equal to 99.50% and a mass purity of the EG is greater than or equal to 99.50%, and a yield of the EGDA is greater than or equal to 99.80% and a mass purity of the EGDA is greater than or equal to 99.90%.

1 Claim, 2 Drawing Sheets

METHODS FOR SEPARATING THE BINARY AZEOTROPIC MIXTURE OF ETHYLENE GLYCOL AND ETHYLENE GLYCOL DIACETATE WITH SULFOLANE ENTRAINER

CROSS-REFERENCE TO RELATED APPLICATION

This application is a continuation-in-part application of International Application No. PCT/CN2023/107635, filed on Jul. 17, 2023, which claims priority of Chinese Patent Application No. 202210842945.2, filed on Jul. 18, 2022, the contents of each of which are entirely incorporated herein by reference.

TECHNICAL FIELD

The present disclosure relates to the field of chemical separation technology, and specifically relates to a method for separating ethylene glycol and ethylene glycol diacetate using sulfolane as an entrainer.

BACKGROUND

Ethylene glycol diacetate (EGDA) is a safe, efficient, and environmentally friendly organic solvent, which is an excellent solvent for cellulose ester and glycerol-based substances, etc., and widely used in a manufacture of paints, printing inks, adhesives, and varnish removers, etc., so the EDGA has a great market demand. Ethylene glycol (EG), as an important raw material and intermediate in the chemical field, has an extremely promising application prospect, which has a wide range of applications especially in polyester, automotive and other industries.

The most common manner of synthesizing the EGDA in industry is a direct esterification of the EG with acetic acid. As the esterification reaction is reversible, a final product system of the reaction inevitably contains water, unreacted EG, and the produced EDGA. The EG and the EDGA form a binary azeotropic mixture, and it is difficult to completely separate EG and the EDGA to obtain high purity products by a conventional distillation separation.

Currently, there are fewer studies on separating a mixed system of the EG and the EDGA. CN 103183609A discloses a preparation method for EG and EDGA using toluene. The method uses the toluene as an extractant to effectively separate the EG and the EDGA by utilizing the feature that EG is difficult to dissolve in toluene while the EDGA is easily to dissolve in the toluene. However, specific operating conditions and purities of the EG and the EDGA after separation are not disclosed. CN 109369396A discloses a method for preparing high purity EGDA by direct esterification. To solve a problem of the formation of the azeotropic mixture of the EG and the EGDA, the method includes adding excess acetic acid to make the EG completely converted during a synthesis process of the EDGA. In this way, although the problem of the formation of the azeotropic mixture of the EG and the EGDA is solved, the excess acetic acid increases an input cost. In addition, two backpack reactors (fixed-bed reactors) containing the mixture of the EG and the acetic acid as well as acid catalysts are added, which accelerates a reaction speed and increases the yield of the EGDA, but the addition of the backpack reactors makes the process complicated and the investment cost increased.

There is therefore a need to provide a simple and efficient method for separating the EG and the EDGA to increase the purity and the yield of the products of the separated EG and the separated EDGA, while reducing the input cost of the entrainer.

SUMMARY

Embodiments of the present disclosure provide a method for separating ethylene glycol (EG) and ethylene glycol diacetate (EDGA) using sulfolane as an entrainer. A yield of the EG is greater than or equal to 99.50% and a mass purity of the EG is greater than or equal to 99.50%, a yield of the EDGA is greater than or equal to 99.80% and a mass purity of the EDGA is greater than or equal to 99.90%. The method includes: (a) obtaining the EG and a mixture of the EDGA and the sulfolane through separating a mixture of the EG and the EDGA under an action of the sulfolane by an extractive distillation tower; (b) obtaining the EDGA and the sulfolane through separating the mixture of the EDGA and the sulfolane by an entrainer recovery tower; and (c) obtaining recycled sulfolane through cooling the sulfolane by a heat exchanger, and mixing the recycled sulfolane with fresh sulfolane and circulating into the extractive distillation tower for recycling. A theoretical plate count of the extractive distillation tower is 18-30, an operating pressure at the top of the extractive distillation tower is 7-8 kPa, a temperature at the top of the extractive distillation tower is 120-130° C., and a temperature at the bottom of the extractive distillation tower is 160-170° C., a feeding position of the mixture of the EG and the EDGA is the 16th-18th theoretical plate of the extractive distillation tower, and a feeding position of the recycled sulfolane and the fresh sulfolane is the 6th-8th theoretical plate of the extractive distillation tower, a ratio of a total mass of the recycled sulfolane and the fresh sulfolane to a mass of the mixture of the EG and the EDGA is (5-7):1; a theoretical plate count of the entrainer recovery tower is 10-15, an operating pressure at the top of the entrainer recovery tower is 3-7 kPa, a temperature at the top of the entrainer recovery tower is 90-100° C., and a temperature at the bottom of the entrainer recovery tower 160-175° C., a feeding position of the mixture of the EDGA and the sulfolane is the 4th-6th plate of the entrainer recovery tower; and a heat exchange temperature difference of the heat exchanger is 65-75° C., and an operating pressure of the heat exchanger is 15-20 kPa.

BRIEF DESCRIPTION OF THE DRAWINGS

The present disclosure will be further illustrated by way of exemplary embodiments, which will be described in detail by means of the accompanying drawings. These embodiments are not limiting, and in these embodiments, the same numbering denotes the same structure, wherein.

DETAILED DESCRIPTION

Figure 1:
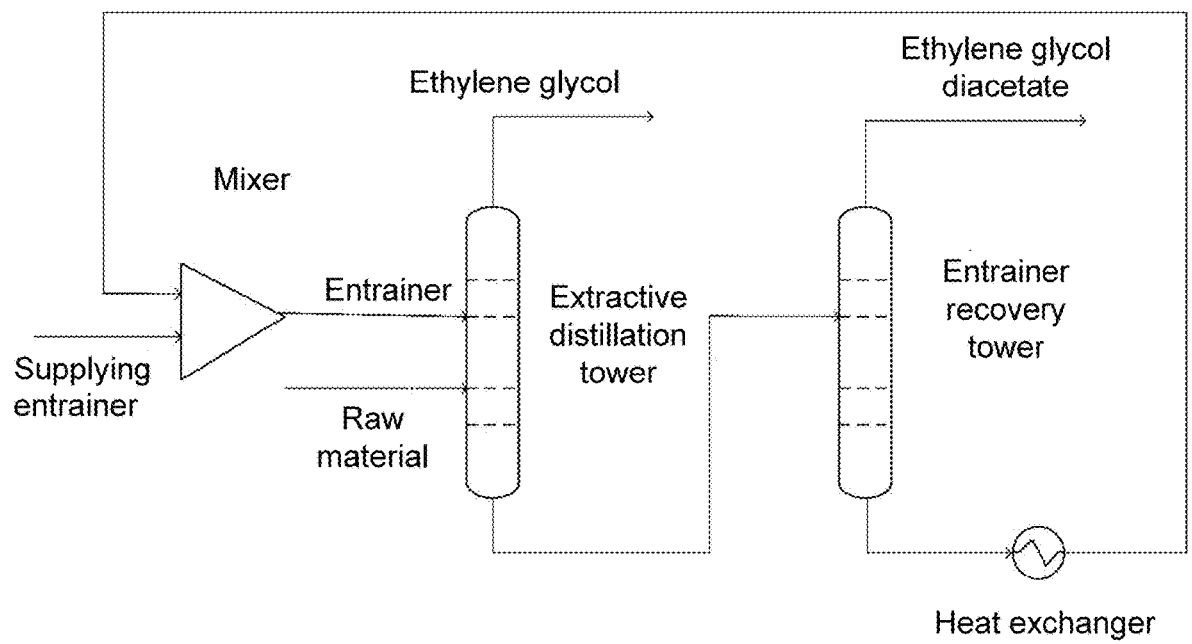
FIG. 1 is a flowchart illustrating a process for separating ethylene glycol and ethylene glycol diacetate using sulfolane as an entrainer according to some embodiments of the present disclosure.

To more clearly illustrate the technical solutions of the embodiments of the present disclosure, the accompanying drawings required to be used in the description of the embodiments are briefly described below. Obviously, the accompanying drawings in the following description are only some examples or embodiments of the present disclosure, and it is possible for those skilled in the art to apply the present disclosure to other similar scenarios in accordance with these drawings without creative labor. Unless obviously obtained from the context or the context illustrates otherwise, the same numeral in the drawings refers to the same structure or operation.

As shown in the present disclosure and the claims, unless the context clearly suggests an exception, the words "one," "a", "an", and/or "the" do not refer specifically to the singular, but also include the plural. In general, the terms "including" and "comprising" only suggest the inclusion of explicitly identified steps and elements that do not constitute an exclusive list, and the method or apparatus may also include other steps or elements.

Pressures involved in the present disclosure are absolute pressures, and unspecified compositions or contents are mass compositions or contents.

At a temperature of 400 K, i.e., 126.85° C., and a pressure of 15 kPa, ethylene glycol (EG) and ethylene glycol diacetate (EGDA) form an azeotropic mixture, and a molar fraction of the EG in the azeotropic mixture is 0.289. The azeotropic mixture has only one boiling point, and a gas composition produced by distillation is the same as a liquid composition, making it difficult to separate high-purity EG and high-purity EGDA from the azeotropic mixture of the EG and the EDGA.

The present disclosure provides a method for facilitating the separation of the EG and the EGDA through a combination of experiments and simulations, finally obtaining the EG and the EGDA with high purity.

Due to a special molecular structure of sulfolane, the boiling point of the sulfolane is much higher than the boiling points of the EG and the EGDA, and the addition of the sulfolane changes an intermolecular interaction between the EG and the EGDA, i.e. the sulfolane has a stronger binding force to the EGDA, thus enabling the separation of the EG. Moreover, the sulfolane does not form the azeotropic mixture with the EG or the EGDA. By selecting the sulfolane as an entrainer, the sulfolane may be well separated from components in the mixed system, so as to realize recycling.

Embodiments of the present disclosure provide a method for separating the EG and the EGDA using sulfolane as the entrainer. The method includes the following operations.

(a) obtaining the EG and the mixture of the EGDA and the sulfolane through separating the mixture of the EG and the EGDA under an action of the sulfolane by an extractive distillation tower.

A tower plate is a place where a gas phase and a liquid phase come into contact for mass and heat transfer in an extractive distillation process. A theoretical plate is an idealized tower plate where the gas phase and the liquid phase are in equilibrium. In some embodiments, the tower plate is a theoretical plate. In some embodiments, a theoretical plate count of the extractive distillation tower is 18-30. In some embodiments, the theoretical plate count of the extractive distillation tower is 19.

In some embodiments, a feeding position of the mixture of the EG and the EGDA is the 16th-18th theoretical plate of the extractive distillation tower. In some embodiments, the feeding position for the mixture of the EG and the EGDA is the 17th theoretical plate of the extractive distillation tower.

In some embodiments, an operating pressure at a top of the extractive distillation tower is 7-8 kPa, a temperature at the top of the extractive distillation tower is 120-130° C., and a temperature at a bottom of the extractive distillation tower is 160-170° C. In some embodiments, the operating pressure at the top of the extractive distillation tower is 8 kPa, the temperature at the top of the extractive distillation tower is 127.21° C., and the temperature at the bottom of the extractive distillation tower is 164.02° C.

After the mixture of the EG and the EGDA is separated by the extractive distillation tower, the EG is separated from the top of the extractive distillation tower, and the mixture of the EGDA and the sulfolane is separated from the bottom of the extractive distillation tower.

(b) obtaining the EGDA and the sulfolane through separating the mixture of the EGDA and the sulfolane by an entrainer recovery tower.

The entrainer recovery tower refers to an extractive distillation tower used to recover the entrainer.

In some embodiments, a theoretical plate count of the entrainer recovery tower is 10-15. In some embodiments, the theoretical plate count of the entrainer recovery tower is 11. In some embodiments, the theoretical plate count of the entrainer recovery tower is 10.

In some embodiments, a feeding position of the mixture of the EGDA and the sulfolane is the 4th-6th plate of the entrainer recovery tower. In some embodiments, the feeding position of the mixture of the EGDA and the sulfolane is the 4th-6th plate of the entrainer recovery tower. In some embodiments, the feed position of the mixture of the EGDA and the sulfolane is the 6th theoretical plate of the entrainer recovery tower.

In some embodiments, an operating pressure at the top of the entrainer recovery tower is 3-7 kPa, a temperature at the top of the entrainer recovery tower is 90-100° C., and a temperature at the bottom of the entrainer recovery tower is 160-175° C. In some embodiments, the operating pressure at the top of the entrainer recovery tower is 3 kPa, the temperature at the top of the entrainer recovery tower is 97.16° C., and the temperature at the bottom of the entrainer recovery tower is 174.57° C.

After the mixture of the EGDA and the sulfolane is separated through the entrainer recovery tower, the EGDA is separated from the top of the entrainer recovery tower, and the sulfolane is separated through the bottom of the entrainer recovery tower.

(c) obtaining recycled sulfolane through cooling the sulfolane by a heat exchanger, and mixing the recycled sulfolane with fresh sulfolane and circulating into the extractive distillation tower for recycling.

The sulfolane separated from the entrainer recovery tower has a relatively high temperature and needs to be cooled down by the heat exchanger before refluxing into the extractive distillation tower for recycling. In some embodiments, a heat exchange temperature difference of the heat exchanger is 65-75° C., and an operating pressure of the heat exchanger is 15-20 kPa. In some embodiments, the heat exchange temperature difference of the heat exchanger is 70.57° C., and the operating pressure of the heat exchanger is 15 kPa.

The recycled sulfolane refers to the sulfolane separated from the entrainer recovery tower that is cooled down. Fresh sulfolane refers to newly added sulfolane. The recycled sulfolane is mixed with the fresh sulfolane to obtain mixed sulfolane and the mixed sulfolane is refluxed into the extractive distillation tower for recycling.

In some embodiments, a feeding position of the recycled sulfolane and the fresh sulfolane is the 6th-8th theoretical plate of the extractive distillation tower. In some embodiments, the feeding position of the recycled sulfolane and the fresh sulfolane is the 8th theoretical plate of the extractive distillation tower.

The recycled sulfolane and the fresh sulfolane are used in a next round of separation of the EG and the EGDA. In some embodiments, a ratio of a total mass of the recycled sulfolane and the fresh sulfolane to a mass of the mixture of the EG and the EGDA is (5-7):1. In some embodiments, the ratio of the total mass of the recycled sulfolane and the fresh sulfolane to the mass of the mixture of the EG and the EGDA is 5.99:1. In some embodiments, the ratio of the total mass of the recycled sulfolane and the fresh sulfolane to the mass of the mixture of the EG and the EGDA is 6.85:1.

The yield of the obtained EG is greater than or equal to 99.50% and the mass purity of the obtained EG is greater than or equal to 99.50%, and the yield of the obtained EGDA is greater than or equal to 99.80% and the mass purity of the obtained EGDA is greater than or equal to 99.90%.

FIG. 1 is a flowchart illustrating a process for separating EG and EGDA using sulfolane as an entrainer according to some embodiments of the present disclosure. As shown in FIG. 1, the EG is separated from a mixture of the EG and the EGDA by an action of the sulfolane by an extractive distillation tower, and the mixture of the EDGA and the sulfolane at a bottom of the extractive distillation tower is further separated by an entrainer recovery tower to obtain the EGDA and the sulfolane, and the sulfolane is then cooled down by a heat exchanger for recycling. Operating conditions for the process shown in FIG. 1 are described above.

Specific embodiments of the present disclosure are illustrated by the following method as an example, which is not meant to be a limitation of the present disclosure: the recycled sulfolane is mixed with the fresh sulfolane and passed through an 8th theoretical plate into the extractive distillation tower, and the mixture of the EG and the EGDA is passed through the 17th theoretical plate into the extractive distillation tower. After passing through the extractive distillation tower, the EG product is recovered from a top of the extractive distillation tower, and the material at the bottom of the extractive distillation tower, i.e., the mixture of the EGDA and the sulfolane, enters the entrainer recovery tower. After extractive distillation in the entrainer recovery tower, the EDGA is obtained from the top of the entrainer recovery tower, and the sulfolane with a high purity is obtained from the bottom of the entrainer recovery tower. The sulfolane is mixed with the fresh sulfolane and refluxed to the extractive distillation tower for recycling.

FIG. 1 only shows the most basic process of the distillation, without involving valves, pumps, reboilers, condensers, etc., which are well known to those skilled in the art.

Beneficial effects that can be achieved by embodiments of the present disclosure include, but are not limited to, the following.
(1) In the present disclosure, the sulfolane is selected as the entrainer to separate the EG and the EGDA by the extractive distillation, which successfully solves a problem of difficult separation of an azeotropic mixture of the EG and the EGDA and obtains the product with a higher purity and a higher yield with a lower process energy consumption.
(2) According to a boiling point of sulfolane and an azeotropic relationship between EG and the EGDA, a better extraction and distillation manner is selected, which not only has a high separation efficiency, saves a reaction time and a production cost investment, but also reduces a loss of the entrainer and a process energy consumption.
(3) Two continuous distillation processes, combining operating conditions and structural parameters such as feeding position and a theoretical plate count, etc., not only reduce a heat load and a cooling load, but also improve the separation efficiency to obtain the EG and the EGDA with high purities, and a mass fraction of the obtained EGDA is more than 99.90%, and a mass fraction of the EG is not less than 99.50%.

The present disclosure is described in detail below in connection with specific embodiments. The following embodiments will be helpful to those skilled in the art to further understand the present disclosure, but do not limit the present disclosure in any way. It should be noted that, for those skilled in the art, a number of adjustments and improvements can be made without departing from the idea of the present disclosure, and these all fall within the scope of protection of the present disclosure.

EMBODIMENTS

Embodiment 1

A mixture of EG and EGDA was separated using sulfolane as an entrainer. A theoretical plate count of an extractive distillation tower was 19, an operating pressure at a top of the extractive distillation tower was 8 kPa, a temperature at the top of the extractive distillation tower was 127.21° C., a temperature at a bottom of the extractive distillation tower was 164.02° C., and a feeding position of the mixture of the EG and the EGDA was the 17th theoretical plate, and a feeding position of the entrainer was the 8th theoretical plate; a theoretical plate count of the entrainer recovery tower was 11, an operating pressure at the top of the entrainer recovery tower was 3 kPa, a temperature at the top of the entrainer recovery tower was 97.16° C., a temperature at the bottom of the entrainer recovery tower was 174.57° C., and a feed position of the mixture of the EGDA and the sulfolane was the 5th theoretical plate; a heat exchange temperature difference of the heat exchanger was 70.57° C., and an operating pressure of the heat exchanger was set to 15 kPa. An extractive distillation separation was performed on the mixture of the EG and the EGDA according to the process of FIG. 1, including the following operations.
  (i) The mixture of the EG and the EGDA whose molar content of the EGDA is greater than 71% was passed from the 17th theoretical plate into the extractive distillation tower.
  (ii) The sulfolane recycled from the entrainer recovery tower was mixed with fresh sulfolane and passed from the 8th theoretical plate into the extractive distillation tower; a ratio of a total mass of the recycled sulfolane and the fresh sulfolane to a mass of the mixture of the EG and the EGDA (noted as an agent-oil ratio) was controlled to be 5.99:1.
  (iii) After an initial extractive distillation, a mixture of the EGDA and the sulfolane separated from the bottom of the extractive distillation tower and the EG separated from the top of the extractive distillation tower were obtained.
  (iv) The mixture of the EGDA and the sulfolane was passed from the 5th theoretical plate into the entrainer recovery tower.
  (v) After performing extractive distillation again, the EGDA separated from the top of the entrainer recovery tower and the sulfolane separated from the bottom of the entrainer recovery tower were obtained.

(vi) After the sulfolane separated from the bottom of the entrainer recovery tower was cooled down by the heat exchanger, the recycled sulfolane was obtained, which was mixed with the fresh sulfolane and refluxed to the extractive distillation tower for recycling.

Operating conditions, raw material composition, an agent-oil ratio, the feeding position, etc. of Embodiment 1 are listed in Table 1, and various product indexes are listed in Table 2.

Embodiment 2

A difference between Embodiment 2 and Embodiment 1 is that, in Embodiment 2, an agent-oil ratio was 6.85:1, and other conditions were essentially the same as in Embodiment 1, an extractive distillation was performed on a mixture of EG and EGDA according to the process of FIG. 1 for separation, and implementation operations of Embodiment 2 were basically consistent with Embodiment 1. Operating conditions of Embodiment 2 are listed in Table 1, and various product indexes are listed in Table 2.

Embodiment 3

A difference between Embodiment 3 and Embodiment 1 is that a theoretical plate count of an entrainer recovery tower in Embodiment 3 was 10, and other conditions were essentially the same as those of Embodiment 1, an extractive distillation was performed on a mixture of EG and EGDA according to the process of FIG. 1 for separation, and implementation operations of Embodiment 3 were basically consistent with Embodiment 1. Operating conditions of Embodiment 3 are listed in Table 1, and various product indexes are listed in Table 2.

Embodiment 4

A difference between Embodiment 4 and Embodiment 1 is that, in Embodiment 4, a feeding position of a mixture of EGDA and the sulfolane was the 6th theoretical plate, and other conditions were essentially the same as those of Embodiment 1, an extractive distillation was performed on a mixture of EG and the EGDA according to the process of FIG. 1 for separation, and implementation steps of Embodiment 4 were basically consistent with Embodiment 1. Operating conditions of Embodiment 4 are listed in Table 1, and various product indexes are listed in Table 2.

Comparative Example 1

Figure 2:
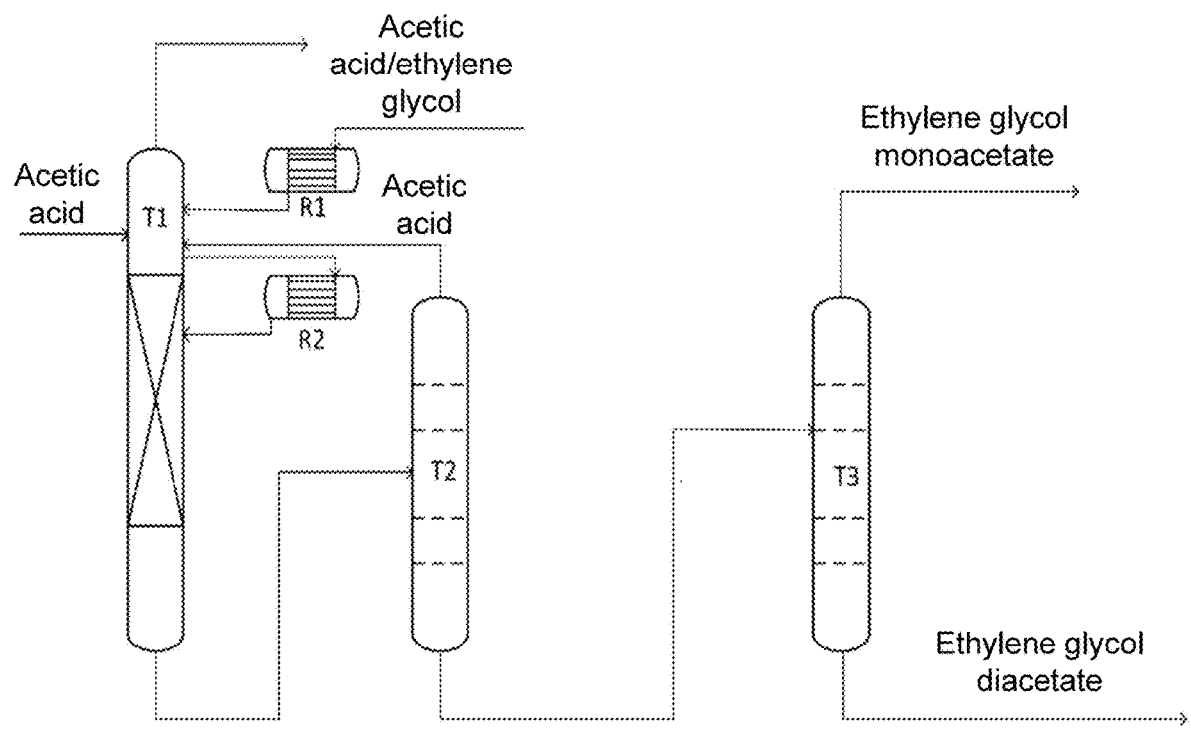
FIG. 2 is a flowchart illustrating a process for preparing high purity ethylene glycol diacetate by direct esterification according to Comparative example 1 of the present disclosure.

FIG. 2 is a flowchart illustrating a process for preparing high purity EGDA by direct esterification according to Comparative example 1 of the present disclosure. As shown in FIG. 2, EG and acetic acid were synthesized into the EGDA in a reactive distillation tower T1 composed of a distillation section, a reaction section, and a stripping section. A specific process was as follows: acetic acid feeding was divided into two strands, one strand was fed from a lower end of the distillation section, and the other strand was mixed with the EG and entered a backpack reactor R1 which contains an acid catalyst. The EG and the acetic acid reacted in the backpack reactor R1 and then entered the reactive distillation tower T1 from an upper end of the reactive distillation tower T1 to continue reaction. The reaction section in the reactive distillation tower T1 was loaded with a catalytic filler, and the EG reacted with the acetic acid to generate the EGDA in the reactive distillation tower T1. T2 was an acetic acid recovery tower, and recycled acetic acid was taken as a raw material and circulated into the reactive distillation tower T1, T3 was a product refining tower, ethylene glycol monoacetate was separated from a top of the product refining tower T3, and the EGDA with a high purity was separated from a bottom of the product refining tower T3.

A specific method for the comparative example 1 was as follows: raw materials including the EG and the acetic acid at a molar ratio of 1:2.40 were preheated to 160° C. The acetic acid feeding was divided into two strands, the first strand was fed from the 5th theoretical plate of T1 at a flow rate of 16.6 kmol/h, and a reflux ratio of the reactive distillation tower T1 was 1.1 and a withdrawal-to-feeding molar ratio of the reactive distillation tower T1 was 0.53. The second strand of the acetic acid with a flow rate of 55.6 kmol/h was mixed with the EG with a flow rate of 27.8 kmol/h and entered a backpack reactor R1 for a partial reaction, which is a fixed-bed reactor equipped with an NKC-9 resin as a catalyst. A temperature of the reactive distillation tower T1 was controlled at 160° C., a reaction pressure of the reactive distillation tower T1 was controlled at 0.12 atm, a space velocity of the reactive distillation tower T1 was 1.5 h−1, and an esterification reaction was performed for 2 h to obtain the EGDA. Comparative example 1 includes following operations.

(i) A reaction mixture of the second strand of the acetic acid and the EG flowed in reverse direction and fully contacted with the first strand of the acetic acid in the reaction distillation tower T1, a liquid phase on a plate of the reaction distillation tower T1 was all lateral withdrawn and entered the backpack reactor R2, so as to promote a complete reaction of the feeding material, and the fully reacted mixture entered the reaction distillation tower T1 for separation.

(ii) Water generated by the reaction in step (i) and a small amount of unreacted acetic acid in step (i) entered the distillation section of the reactive distillation tower T1 for separation, then condensed in a condenser at the top of the reactive distillation tower T1, and then withdrawn from the top of the reactive distillation tower T1, while the EGDA, a small amount of the ethylene glycol monoacetate, and an excess amount of the acetic acid are withdrawn from the kettle of the reactive distillation tower T1.

(iii) The EGDA, the small amount of the ethylene glycol monoacetate, and the excess acetic acid were fed from the 15th plate of the acetic acid recovery tower T2 and separated, and the acetic acid with a high purity separated at the top of the acetic acid recovery tower T2 was returned to the reactive distillation tower T1 to be recycled as a raw material.

(iv) The discharge from the kettle of the acetic acid recovery tower T2 was the EGDA with a high concentration, a small amount of the ethylene glycol monoacetate, and a small amount of unreacted EG, the discharge from the kettle of the acetic acid recovery tower T2 was fed from the 15th plate of the product refining tower T3 for refining, and the EGDA was obtained after separation.

Operating conditions, raw material composition, an agent-oil ratio, a feeding position, etc., for Comparative example 1 are listed in Table 1, and various product indexes are listed in Table 2.

Comparative Example 2

A difference between the comparative example 2 and the comparative example 1 is that, in the comparative example 2, a molar ratio of EG and an acetic acid was 1:2.60, and a temperature of the reactive distillation tower T1 was controlled to be 150° C. Other conditions and operations were kept the same as the conditions and steps of the comparative example 1, and EGDA with a high purity was prepared according to the process of FIG. 2. Operating conditions of the comparative example 2 are listed in Table 1, and various product indexes are listed in Table 2.

Comparative Example 3

A basic process and parameters of the comparative example 3 are the same as embodiment 1, except that benzene was used as an entrainer. Benzene was a light component relative to EG and EGDA and was therefore separated by an extractive distillation tower. The entrainer, benzene, entered the extractive distillation tower from a lower portion of the tower and the raw material entered the extractive distillation tower from an upper portion of the tower. As shown in Table 1, a feeding position of the entrainer benzene was the 17th theoretical plate of the extractive distillation tower, while a feeding position of the raw material was the 5th theoretical plate of the extractive distillation tower. As the entrainer benzene was the light component, the EGDA product was separated from a kettle of the extractive distillation tower, and a mixture of the benzene, the EG, and the remaining EGDA is discharged from the top of the extractive distillation tower and then fed into an entrainer recovery tower for recycling entrainer benzene. Various product indexes obtained in comparative example 3 are listed in Table 2.

TABLE 1

| | items | Comparative example 1 | Comparative example 2 | Comparative example 3 | Embodiment 1 | Embodiment 2 | Embodiment 3 | Embodiment 4 |
|---|---|---|---|---|---|---|---|---|
| | Molar ratio of raw material composition (EG/EGDA or EG/HAC) | 1:2.40 | 1:2.60 | 1:2.46 | 1:2.46 | 1:2.46 | 1:2.46 | 1:2.46 |
| Extractive Distillation Tower/ acetic acid recovery tower T2 | Theoretical plate count | 24 | 24 | 19 | 19 | 19 | 19 | 19 |
| | Entrainer feeding position | — | — | 17 | 8 | 8 | 8 | 8 |
| | Raw material feeding position | 15 | 15 | 5 | 17 | 17 | 17 | 17 |
| | Tower top pressure, kPa | 101 | 101 | 8 | 8 | 8 | 8 | 8 |
| | Tower bottom pressure, kPa | 101 | 101 | 8.15 | 8.15 | 8.15 | 8.15 | 8.15 |
| | Temperature at the top of the tower, ° C. | 160 | 150 | 16.90 | 127.21 | 127.21 | 127.21 | 127.21 |
| | Temperature at the bottom of the tower, ° C. | 160 | 150 | 117.14 | 164.02 | 164.02 | 166.20 | 164.02 |
| | Feeding amount of entrainer, kg/h | — | — | 84120.6 | 84120.6 | 96127.6 | 84120.6 | 84120.6 |
| | Feeding amount of raw material, kg/h | — | — | 14037.6 | 14037.6 | 14037.6 | 14037.6 | 14037.6 |
| | agent-oil ratio | — | — | 5.99 | 5.99 | 6.85 | 5.99 | 5.99 |
| | reflux ratio | 2.8 | 2.8 | 2.25 | 2.25 | 2.25 | 2.25 | 2.25 |
| Entrainer Recovery Tower/ product refining tower T3 | Theoretical plate count | 35 | 35 | 11 | 11 | 11 | 10 | 11 |
| | Feeding position | 15 | 15 | 5 | 5 | 5 | 5 | 6 |
| | Tower top pressure, kPa | 101 | 101 | 3 | 3 | 3 | 3 | 3 |
| | Tower bottom pressure, kPa | 101 | 101 | 4.5 | 4.5 | 4.5 | 4.5 | 4.5 |

TABLE 1-continued

| | items | Comparative example 1 | Comparative example 2 | Comparative example 3 | Embodiment 1 | Embodiment 2 | Embodiment 3 | Embodiment 4 |
|---|---|---|---|---|---|---|---|---|
| | Temperature at the top of the tower, °C. | 160 | 150 | −2.73 | 97.16 | 97.16 | 97.16 | 97.10 |
| | Temperature at the bottom of the tower, °C. | 160 | 150 | 111.64 | 174.57 | 173.64 | 173.64 | 174.57 |
| | reflux ratio | 3.2 | 3.2 | 6 | 6 | 6 | 6 | 6 |
| Heat exchanger | Operating temperature, °C. | — | — | — | 104 | 104 | 104 | 104 |
| | Operating pressure, kPa | — | — | — | 15 | 15 | 15 | 15 |
| Phase splitter | Operating temperature, °C. | — | — | — | — | — | — | — |
| | Operating pressure, kPa | — | — | — | — | — | — | — |

Note:
EG-ethylene glycol, EGDA-ethylene glycol diacetate, HAC-acetic acid

TABLE 2

| Item | Comparative example 1 | Comparative example 2 | Comparative example 3 | Embodiment 1 | Embodiment 2 | Embodiment 3 | Embodiment 4 |
|---|---|---|---|---|---|---|---|
| Molar purity of EGDA, % | — | — | 99.90 | 99.90 | 99.90 | 99.90 | 99.90 |
| Mass purity of EGDA, wt % | — | — | 99.96 | 99.92 | 99.92 | 99.92 | 99.92 |
| Yield of EGDA, % | 98.27 | 99.92 | 34.62 | 99.91 | 99.91 | 99.84 | 99.91 |
| Molar purity of EG, % | — | — | 38.31 | 99.80 | 99.80 | 99.80 | 99.80 |
| Mass purity of EG, wt % | — | — | 20.87 | 99.55 | 99.55 | 99.54 | 99.55 |
| Yield of EG, % | 98.37 | 99.92 | — | 99.86 | 99.86 | 99.58 | 99.86 |
| Total heat load, MW | — | — | 115.35 | 8.86 | 8.86 | 8.75 | 8.86 |
| Total cooling load, MW | — | — | 117.54 | 8.88 | 8.88 | 8.88 | 8.88 |

As shown in Table 2, in Embodiments 1-4, the mixture of the EG and the EGDA was separated utilizing the method of the present disclosure, and the obtained EGDA has a purity of more than 99.90 wt %, and the obtained EG has a purity of more than 99.50 wt %. Compared with the comparative examples 1-2, the embodiments 1-4 uses the extractive distillation or an azeotropic distillation, which achieves a better separation effect of the mixture of the EG and the EGDA. In this way, on the one hand, the yield of the product and the purity of the product are clarified, on the other hand, the purity of the product is higher, the yield is higher, and an energy consumption is lower. At the same time, using aromatic entrainer benzene and adopting a double-tower extractive distillation process in comparative example 3, the benzene is unable to accomplish a task of separating the mixture of the EG and the EGDA, and in the situation where key process parameters are exactly the same as in Example 1, using benzene as entrainer, the obtained EGDA product has a purity of 99.90%, but a single cycle yield is only 34.62%, and an EG product with high purity is unable to be obtained. In addition, as the entrainer benzene is the light component, which is discharged from the top of the tower, it inevitably requires more energy consumption under a same reflux ratio condition, as shown in Table 1, and a total cooling load and a total heat load of the comparative example 3 are 13.24 and 13.02 times that of the embodiment 1, respectively.

It is experimentally verified that the method of the present disclosure is unaffected by composition of the mixture of the EG and the EGDA, and both the EG with a high purity and the EGDA with a high purity are able to be obtained.

The foregoing is only a preferred embodiment of the present disclosure, and is not intended to limit the present disclosure, and any modifications, equivalent substitutions, and improvements, etc., made within the spirit and principles of the present disclosure shall be included in the scope of protection of the present disclosure.

What is claimed is:

1. A method for separating ethylene glycol and ethylene glycol diacetate using sulfolane as an entrainer, wherein a yield of the ethylene glycol is greater than or equal to 99.50% and a mass purity of the ethylene glycol is greater than or equal to 99.50%, a yield of the ethylene glycol diacetate is greater than or equal to 99.80% and a mass purity of the ethylene glycol diacetate is greater than or equal to 99.90%, and the method comprises:
    (a) obtaining the ethylene glycol and a mixture of the ethylene glycol diacetate and the sulfolane through separating a mixture of the ethylene glycol and the ethylene glycol diacetate under an action of the sulfolane by an extractive distillation tower;
    (b) obtaining the ethylene glycol diacetate and the sulfolane through separating the mixture of the ethylene glycol diacetate and the sulfolane by an entrainer recovery tower; and
    (c) obtaining recycled sulfolane through cooling the sulfolane by a heat exchanger, mixing the recycled sulfolane with fresh sulfolane and circulating into the extractive distillation tower for recycling;
    wherein a theoretical plate count of the extractive distillation tower is 18-30, an operating pressure at a top of the extractive distillation tower is 7-8 kPa, a temperature at the top of the extractive distillation tower is 120-130° C., and a temperature at a bottom of the extractive distillation tower is 160-170° C.,
    a feeding position of the mixture of the ethylene glycol and the ethylene glycol diacetate is the 16th-18th theoretical plate of the extractive distillation tower, and a feeding position of the recycled sulfolane and the fresh sulfolane is the 6th-8th theoretical plate of the extractive distillation tower,
    a ratio of a total mass of the recycled sulfolane and the fresh sulfolane to a mass of the mixture of the ethylene glycol and the ethylene glycol diacetate is (5-7):1;
    a theoretical plate count of the entrainer recovery tower is 10-15, an operating pressure at the top of the entrainer recovery tower is 3-7 kPa, a temperature at the top of the entrainer recovery tower is 90-100° C., and a temperature at the bottom of the entrainer recovery tower is 160-175° C.,
    a feeding position of the mixture of the ethylene glycol diacetate and the sulfolane is the 4th-6th plate of the entrainer recovery tower; and
    a heat exchange temperature difference of the heat exchanger is 65-75° C., and an operating pressure of the heat exchanger is 15-20 kPa.

* * * * *